(12) United States Patent
Shimmick et al.

(10) Patent No.: US 6,592,574 B1
(45) Date of Patent: Jul. 15, 2003

(54) HYDRATION AND TOPOGRAPHY TISSUE MEASUREMENTS FOR LASER SCULPTING

(75) Inventors: John Karl Shimmick, Belmont, CA (US); Charles R. Munnerlyn, San Jose, CA (US); George Caudle, San Jose, CA (US); Terrance N. Clapham, Jamestown, CA (US)

(73) Assignee: VISX, Incorporated, Santa Clara, CA (US)

( * ) Notice: Subject to any disclaimer, the term of this patent is extended or adjusted under 35 U.S.C. 154(b) by 253 days.

(21) Appl. No.: 09/626,732

(22) Filed: Jul. 27, 2000

Related U.S. Application Data
(60) Provisional application No. 60/146,231, filed on Jul. 28, 1999.

(51) Int. Cl.[7] .............................................. A61B 18/18
(52) U.S. Cl. .................................. 606/4; 606/5; 606/10; 606/12; 351/206; 351/211; 351/212
(58) Field of Search ........................... 604/20, 289, 294; 250/365, 370, 461.1; 356/57; 600/310, 473, 476; 607/94; 606/4–6, 10–13, 17; 351/200, 206, 211–221

(56) References Cited

U.S. PATENT DOCUMENTS

| | | | |
|---|---|---|---|
| 3,169,459 A | 2/1965 | Friedberg et al. | 95/18 |
| 4,019,813 A | 4/1977 | Cornsweet et al. | 351/14 |
| 4,412,543 A | 11/1983 | Vassiliadis et al. | 128/633 |
| 4,459,027 A | 7/1984 | Kafri et al. | 356/376 |
| 4,606,623 A * | 8/1986 | Schachar | 351/212 |
| 4,669,466 A | 6/1987 | L'Esperance | 128/303.1 |
| 4,692,003 A | 9/1987 | Adachi et al. | 351/212 |
| 4,721,379 A | 1/1988 | L'Esperance | 351/212 |
| 4,761,071 A | 8/1988 | Baron | 351/212 |
| 4,994,059 A | 2/1991 | Kosa et al. | 606/12 |
| 4,995,716 A | 2/1991 | Warnicki et al. | 351/212 |
| 5,159,361 A | 10/1992 | Cambier et al. | 351/212 |

(List continued on next page.)

FOREIGN PATENT DOCUMENTS

| | | | |
|---|---|---|---|
| WO | WO 99/12467 | 3/1999 | A61B/3/117 |
| WO | WO 99/20173 | 4/1999 | A61B/3/14 |
| WO | WO 99/23936 | 5/1999 | A61B/3/00 |
| WO | WO 99/55216 | 11/1999 | |
| WO | WO 00/10449 | 3/2000 | A61B/3/107 |

OTHER PUBLICATIONS

Campos, Mauro et al. *Ablation Rates and Surface Ultrastructure of 193 nm Excimer Laser Keratectomies. Inv. Ophtha. & Vis. Sci.*, Jul. 1993, vol. 34, 8, pp. 2493–2500.

Dougherty, M.D., Paul J., et al. *Excimer Laser Ablation Rate and Corneal Hydration. Amer. J. Ophthalmol.*, Aug. 1994:118:169–176.

Ediger, MN. *Excimer–Laser–Induced Fluorescence of Rabbit Cornea: Radiometric Measurement Through the Cornea. Lasers Surg. Med.* Nov. 1991:11:93–98.

(List continued on next page.)

*Primary Examiner*—Linda C. M. Dvorak
*Assistant Examiner*—A. Farah
(74) *Attorney, Agent, or Firm*—Townsend Townsend & CrewLLP; Mark D. Barrish, Esq.

(57) ABSTRACT

Improved systems, devices, and methods measure and/or change the shape of a tissue surface, particularly for use in laser eye surgery. Fluorescence of the tissue may occur at and immediately underlying the tissue surface. The excitation energy can be readily absorbed by the tissue within a small tissue depth, and may be provided from the same source used for photodecomposition of the tissue. Changes in the fluorescence spectrum of a tissue correlate with changes in the tissue's hydration.

28 Claims, 11 Drawing Sheets

U.S. PATENT DOCUMENTS

| | | | | |
|---|---|---|---|---|
| 5,350,375 A | | 9/1994 | Deckelbaum et al. | 606/7 |
| 5,406,342 A | * | 4/1995 | Jongsma | 351/212 |
| 5,505,724 A | | 4/1996 | Steinert | 606/5 |
| 5,634,920 A | * | 6/1997 | Hohla | 606/12 |
| 5,646,791 A | | 7/1997 | Glockler | 359/831 |
| 5,701,902 A | * | 12/1997 | Vari et al. | 128/664 |
| 5,713,892 A | | 2/1998 | Shimmick | 606/5 |
| 5,822,035 A | * | 10/1998 | Bille | 351/215 |
| 5,827,264 A | | 10/1998 | Hohla | 606/5 |
| 6,019,755 A | * | 2/2000 | Steinert | 606/5 |
| 6,293,939 B1 | | 9/2001 | Steinert | |

OTHER PUBLICATIONS

Phillips, Andrew F., et al. *Laser–Induced Fluorescence During Photorefractive Kertectomy: A Method for Controlling Epithelial Removal.* Amer. Jour. Ophthal. Jan. 1997:123:42–47.

Seiler, M.D., Theo et al. *Ablation Rate of Human Corneal Epithelium and Bowman's Layer with the Excimer Laser (193 nm).* Retractive & Corneal Surg. Mar./Apr. 1990:6:99–102.

Tuft, Stephen et al. *Characterization of the Fluorescence Spectra Produced by Excimer Laser Irradiation of the Cornea.* Inv. Ophthalm. Vis. Sci. Aug. 1990:31:8:1512–1518.

BioShape AG. Application for Refraktive Surgery:*EyeShape by BioShape*, pages from website located at: http//:www.bioshape.com/eyeshape/eyeshape.htm, .../corneal.htm, .../thebiosh.htm, and .../example.htm.

* cited by examiner

HYDRATION AND TOPOGRAPHY TISSUE MEASUREMENTS FOR LASER SCULPTING

CROSS-REFERENCES TO RELATED APPLICATIONS

The present application is a regular patent application of and claims the benefit of priority from U.S. Provisional Patent Application Ser. No. 60/146,231 filed Jul. 28, 1999, the full disclosure of which is. incorporated herein by reference.

BACKGROUND OF THE INVENTION

1. Field of the Invention

The present invention relates generally to medical devices, systems, and methods. More particularly, the present invention relates to the measurement of a tissue surface such as the surface of the cornea. The invention allows measurement of the tissue surface shape, and/or can provide a measurement of the hydration of the tissue.

Measurements of the surfaces of the eye are useful in diagnosing and correcting vision disorders. Refractive vision errors such as nearsightedness, farsightedness and astigmatism may be corrected surgically. Photorefractive keratectomy (PRK) and phototherapeutic keratectomy (PTK) employ optical beam delivery systems for directing a pattern of laser energy to a patient's eye in order to selectively ablate corneal tissue to reform the shape of the cornea and improve vision. These techniques generally sculpt the corneal tissue to alter the optical characteristics of the eye. Measurement of the eye surface may enhance the accuracy of the sculpting procedure, and could be used to verify that resculpting is proceeding as intended.

Known laser eye surgery techniques often rely on an analysis of the patient's vision to calculate a predetermined pattern of the laser energy so as to effect a desired change in the optical characteristics of the eye. These calculations often assume that the corneal tissue ablates uniformly. The laser pattern is often defined by a beam formed as a series of discrete laser pulses, and known pulse pattern calculation algorithms often assume that each pulse of laser energy removes corneal tissue to a uniform depth, so that the size, location, and number of pulses distributed across the target region of the corneal tissue determine the characteristics of the resculpting. Such techniques work quite well, particularly for eyes having "regular" refractive errors such as myopia, hyperopia, astigmatism, and the like. However, work in connection with the present invention has suggested that pulse ablation depths are not always uniform. Additionally, treatment of irregular corneas can benefit significantly from an accurate measurement of the corneal surface shapes. Hence, a combination of refractive resculpting capabilities with techniques for accurately measuring the shape of the eye would appear to be quite promising.

Current techniques for measuring the eye during surgery suffer from various limitations. Generally, known techniques for measuring the shape of an eye measure either light that is reflected from the surface of the eye, light that scatters from the eye, or the fluorescence of a dye that is applied to the eye. Unfortunately, the surface of the cornea becomes rough during surgery. Light that is reflected from the eye is unevenly scattered, often making measurements with reflected light difficult and inaccurate. Many techniques that employ scatter from the surface of the eye also have limited accuracy because light does not scatter evenly from the rough eye surface. Applying a fluorescent dye to the eye can lead to an inaccurate measurement of the surface shape because it is the shape of the dye covering the eye, rather than the eye itself, that is measured. Also, applying a dye to a tissue structure of the eye can delay a surgical procedure, and generally changes the hydration of the eye.

Hydration of the eye can also be difficult to measure accurately using known techniques, particularly during an ablation procedure. As both the depth of an ablation and the shape of tissue removed can vary with the water content of the tissue, known laser eye surgery techniques often include provisions to control the moisture in the corneal tissue before and/or during the procedure. Nonetheless, variations in moisture content, both locally (on different areas of the same target tissue) and between different patients (in different climates, or the like) can occur, potentially leading to significant differences between the intended resculpting and the actual change in the shape of the corneal tissue.

In light of the above, it would generally be desirable to provide improved tissue surface measurement and ablation systems, devices, and methods. It would be beneficial if the improved surface measurement techniques were suitable for integration with known laser eye surgery systems, particularly if these techniques could provide diagnostic information before, and/or feedback information during, a corneal resculpting procedure. It would further be beneficial to provide information on the shape and/or hydration of the corneal surface itself, and if these measurements could be used to modify the resculpting laser energy pattern for that corneal tissue surface. Some or all of these objectives are satisfied by the devices described below.

2. Description of the Background Art

Techniques for measuring the surface of the cornea using a film covering the cornea are described in U.S. Pat. Nos. 3,169,459; 4,761,071; 4,995,716; and 5,159,361. Moire techniques using specular reflection from the surface of the eye or fluorescent dyes are described in U.S. Pat. Nos. 4,692,003; 4,459,027; and 5,406,342. A technique for measuring the surfaces of the cornea using a vidicon tube is described in U.S. Pat. No. 4,019,813.

A technique for measuring the eye during laser eye surgery is described in U.S. patent application Ser. No. 09/083,773, entitled "Systems and Methods for Imaging Corneal Profiles", filed on May 22, 1998. Techniques for combining corneal topography and laser eye surgery are described in U.S. Pat. No. 4,669,466 and 4,721,379, respectively entitled "Method And Apparatus For Analysis And Correction Of Abnormal Refractive Errors Of The Eye" and "Apparatus For Analysis And Correction Of Abnormal Refractive Errors Of The Eye." An exemplary system and method for treating irregular corneas is described in U.S. patent application Ser. No. 09/287,322, entitled "Offset Ablation Profiles For Treatment Of Irregular Astigmatism", filed on Apr. 7, 1999 now U.S. Pat. No. 6,245,059.

Each of the above references is herein incorporated by reference in its entirety.

SUMMARY OF THE INVENTION

The present invention generally provides improved systems, devices, and methods for measuring and/or changing the shape of a tissue surface, particularly during laser eye surgery. The invention generally takes advantage of fluorescence of the tissue at and immediately underlying the tissue surface. Preferably, the excitation energy will be in a form which is readily absorbed by the tissue within a small tissue depth from the surface to be measured, thereby enhancing the resolution of any surface topography measurements. Conveniently, the excitation light energy to induce this fluorescence may be provided by the same source used for photodecomposition of the tissue. Hence, these measurement techniques may be readily incorporated into laser eye surgery systems and procedures, providing surface shape information before, during, and/or after a resculpting of the cornea. The invention may optionally take advantage of changes in the fluorescence spectrum of a tissue which occur in correlation with changes in the tissue's hydration. Such hydration measurements may be used to revise the ablation algorithm locally and/or globally throughout the treatment region, enhancing the accuracy of the ablation energy pattern by compensating for the changes in ablation rates due to variation in hydration. Alternate hydration measurements may be based on thin film ellipsometry using techniques developed for integrated circuit production to measure a thickness of the fluid film covering the corneal tissue surface.

In a first aspect the invention provides a method for measuring a surface topography of a surface of a tissue. The method comprises exposing the tissue to an excitation light energy so that the tissue produces a fluorescent light energy. The fluorescent light energy is measured from the fluorescent tissue, and the surface topography of the surface is determined using the measured fluorescent light energy.

Often times, the fluorescent tissue will be imaged onto a detector which is responsive to the fluorescent light energy. Preferably, the excitation light energy will be selected so that an amount in a range from about 50 to 100% of the excitation light energy is absorbed within a tissue depth equal to a resolution of the surface topography. The excitation light energy may be projected onto the tissue in a controlled irradiance pattern. The surface topography can be calculated from measured intensities of the fluorescent light energy.

A variety of excitation light energy wavelengths might be used, depending on the desired application. Generally, ultraviolet wavelengths in a range from about 150 to 400 nm, and more preferably from about 190 to about 220 nm are preferred for measuring exposed tissue surfaces. Similarly, while many wavelengths of fluorescent light energy can be measured, the measured fluorescent light energy from the tissue will generally be from about 250 to about 500 nm, the measured fluorescent light energy preferably being in a range from about 300 to 450 nm. Suitable excitation light energy sources include visible, ultraviolet, and infrared lasers, deuterium lamps, arc lamps, and the like. Typically, the excitation energy will have a different wavelength than the measured fluorescent light energy, allowing the excitation energy to be easily blocked from reaching the detector.

In another aspect, the invention provides a method for measuring a surface topography of an exposed surface of a corneal tissue. The method comprises making an excitation light energy with a wavelength in a range of about 190 to 220 nm. The tissue is exposed to the excitation light energy to induce a fluorescent light energy from the tissue. The fluorescent light energy has a wavelength in a range of about 300 to 450 nm. The excitation light energy is projected onto the tissue in a controlled irradiance pattern. From about 50 to 100% of the excitation light energy is absorbed by the tissue within a 3 $\mu$m tissue depth from the exposed surface. The fluorescent light energy is imaged onto a detector responsive to the fluorescent light energy. An intensity of the fluorescent light energy is measured with the detector, and the surface topography is calculated from the measured intensity of the fluorescent light energy.

In another aspect, the invention provides a method for laser sculpting a region of a surface of a tissue. The method comprises directing an ablative light energy toward the surface, and inducing a fluorescent light energy from the tissue with the ablative light energy. An intensity of the fluorescent light energy is measured, and the shape of the exposed surface is determined using the measured intensity. The tissue is ablated with a pulsed beam of the ablative light energy.

In yet another aspect, the invention provides a system for measuring a surface topography of an exposed surface of a corneal tissue. The system comprises a light source generating an excitation light energy to induce a fluorescent light energy from the tissue. The excitation light energy has a wavelength in a range of about 190 to 220 nm, wherein about 50 to 100% of the excitation light energy is absorbed within a 3 $\mu$m tissue depth so as to provide no more than 3 $\mu$m resolution of the surface topography. A projection system projects the excitation light energy onto the tissue in a controlled irradiance pattern. An imaging system images the fluorescent light energy emitted by the tissue, and a spatially resolved detector measures an intensity of the fluorescent light energy emitted by the tissue in wavelength range of about 300 to 450 nm. A processor calculates the surface topography from the intensity of the fluorescent light measured by the detector.

In another system aspect, the invention provides a laser system for sculpting a region on an exposed tissue surface to a desired surface topography. The tissue has a threshold of ablation, and the system comprises a laser making a pulsed beam of an excitation light energy having an ablative wavelength that induces fluorescent light energy from the tissue. An optical delivery system delivers the light energy to the eye in a controlled manner to sculpt the surface. An imaging system images the fluorescent light energy, and a detector measures an intensity of the imaged fluorescent light energy to determine the shape of the exposed tissue.

In addition to topography measurements and topography-based laser ablation systems and methods, the invention also provides hydration measurement devices, systems, and methods for both measuring and selectively ablating tissues which are sensitive to their water content.

In a first hydration aspect, the invention provides a system for measuring hydration of a tissue. The system comprises a light source directing an excitation light toward the tissue so that the tissue generates fluorescent light. A fluorescent light sensor is in an optical path of the fluorescent light from the tissue. The sensor generates a signal indicating the fluorescent light. A processor is coupled to the sensor, the processor generating a hydration signal indicating the hydration of the tissue from the fluorescent light signal.

Many times, an ablation energy delivery system will be coupled to the processor. The delivery system will direct an ablative energy toward the tissue, and the processor will vary the ablative energy in response to the hydration signal. The tissue will typically comprise a corneal tissue of an eye, and the delivery system may comprise an optical delivery system transmitting photoablative laser energy toward the corneal tissue so as to selectively alter an optical characteristic of the eye. The processor may vary a quantity of change in the optical characteristic of the eye in response to the hydration signal. For example, the processor may vary a diopter value of the resculpting procedure in response to overall tissue hydration. Alternatively, the processor may vary the shape of the ablation by altering the ablative energy pattern so as to compensate for local differences in hydration across the target region of the corneal tissue. In some embodiments, an output device coupled to the processor may simply show a display in response to the hydration signal.

Generally, an intensity of the fluorescent spectrum of the tissue will vary with the hydration, so that the signal indicates an intensity of the fluorescent light at a first frequency. The processor will often normalize the signal using an intensity of the fluorescent light at a second frequency. The second frequency may be disposed adjacent a crossover point of a plurality of fluorescence spectrums of the tissue at different hydrations, so that the intensity of the fluorescent light at the second frequency is less sensitive to hydration than at the first frequency. Hence, the processor may calculate the hydration as a function of the relative intensity of the first frequency relative to the second frequency.

The sensor will often comprise a spectrometer, and imaging optics will often direct the fluorescent light along the optical path from the tissue to the spectrometer. The imaging optics may form an image of a target area of the tissue adjacent the spectrometer sensing surface.

In another aspect, the invention provides a system for use in an apparatus for resculpting a corneal tissue of an eye. The apparatus directs a pattern of light energy from a laser under the direction of a processor to effect a desired change in an optical characteristic of the eye. The system comprises a sensor coupled to the processor. The sensor generates a signal indicating hydration of the corneal tissue. An adjustment module of the processor varies the pattern in response to the hydration signal from the sensor.

In another aspect, the invention provides a method for measuring hydration of a tissue. The method comprises directing an excitation light energy toward the tissue so that the tissue generates fluorescent light. The fluorescent light is sensed, and the hydration of the tissue is calculated using the sensed fluorescent light.

In yet another aspect, the invention provides a compensation method for use in a procedure for resculpting a corneal tissue of an eye. The resculpting procedure will selectively direct a pattern of laser energy toward the eye to effect a predetermined change in an optical characteristic of the eye. The compensation method comprises sensing a hydration of the tissue. The pattern of laser energy is adjusted in response to the sensed hydration.

Typically, the hydration is sensed by directing an excitation light toward the tissue so that the tissue generates fluorescent light. An intensity of the fluorescent light is measured at a first frequency relative to a second frequency. The hydration of the tissue is calculated using the measured relative intensity. The ablation rate may be estimated for the calculated hydration, and the pattern adjusting step varied in response to this estimated ablation rate. Conveniently, the excitation light may be generated by the same source providing the ablative laser energy. Alternatively, the hydration may be sensed by measuring a thickness of a fluid film over the surface of the eye using ellipsometry.

In another method aspect, the invention provides a method for sculpting of a corneal tissue of an eye to effect a desired change in an optical property. The method comprises sensing hydration of the corneal tissue and determining a desired change in shape of the eye in response to the hydration, and in response to the desired change in optical property. A pattern of laser energy is planned for directing toward the corneal tissue, so at to effect the determined change in shape.

The desired change in optical quality will often be determined while the eye has a first hydration, optionally a normal hydration for the ambient conditions. The change in optical quality may be determined using any of a variety of standard vision diagnostic systems. Wavefront sensor systems now being developed may also be beneficial for determining a desired change in an optical property, and still further alternative topography and/or tomography systems may also be used. Regardless, rather than simply determining the desired change in shape of the eye from such measurements alone, the desired sculpting or ablation shape can also be based in part on the hydration of the eye.

Corneal tissue may increase in thickness by up to 50% due to changes in hydration by the time an ablation begins. Such swelling of the eye before and/or during an ablation procedure can be problematic, as the effective sculpting of the eye after hydration returns to normal can be significantly different than the intended result. More specifically, therapeutic compounds applied to the eye, incising of the eye to expose stromal tissue for a LASIK ablation procedure, and/or other standard techniques for preparation of and performing corneal sculpting may cause corneal tissue to swell like a sponge, significantly increasing both the hydration and thickness of corneal tissues. To effect the desired change in optical properties, a total depth of corneal tissue removal from the eye should be increased to compensate for such swelling of the corneal tissues.

In many embodiments, the corneal tissues may increase in thickness in a range from about 10% to about 50% with the increase in hydration. A first tissue removal depth which would effect the desired change in optical property of the eye when the eye has a first hydration (for example, at a normal hydration) may be increased by between about 10% and 50% when the eye has an enhanced second hydration (for example, during corneal ablation procedures). In many embodiments, the increase in tissue removal depth will compensate for swelling of the tissue, the increase depth percentage often being very roughly equal to the percentage of the swelling of the corneal tissue.

DESCRIPTION OF THE SPECIFIC EMBODIMENTS

The present invention is generally directed to structures, systems, and methods of measuring and/or changing the shape of a tissue structure. This invention includes an improved technique for measuring a tissue. The measurement is often of the shape of a tissue structure. Alternatively, the measurement may be of a hydration of a region of tissue to be ablated.

During tissue reshaping the tissue measurement can be used to control the tissue reshaping process. As an example, surgery of the cornea of an eye reshapes the cornea to correct vision errors to replace eyeglasses and contact lenses. It is desirable to measure the shape of the eye during surgery to ensure that the eye has been changed to an intended shape. It is also desirable to measure the hydration of the eye to ensure that the laser energy pattern delivered to the eye is correct for the actual hydration of the eye.

Surgical procedures that reshape a corneal tissue of the eye to correct vision disorders include photorefractive keratectomy (PRK), phototherapeutic keratectomy (PTK), and laser assisted in situ keratomileusis (LASIK). The invention is particularly useful for performing corneal ablation in LASIK, PRK, and PTK procedures but will also be useful for removing an epithelial layer prior to stromal ablation in such procedures. For convenience, the following discussion will be directed at stromal ablation, but the teachings are also useful for removing epithelial tissue.

Figure 1:
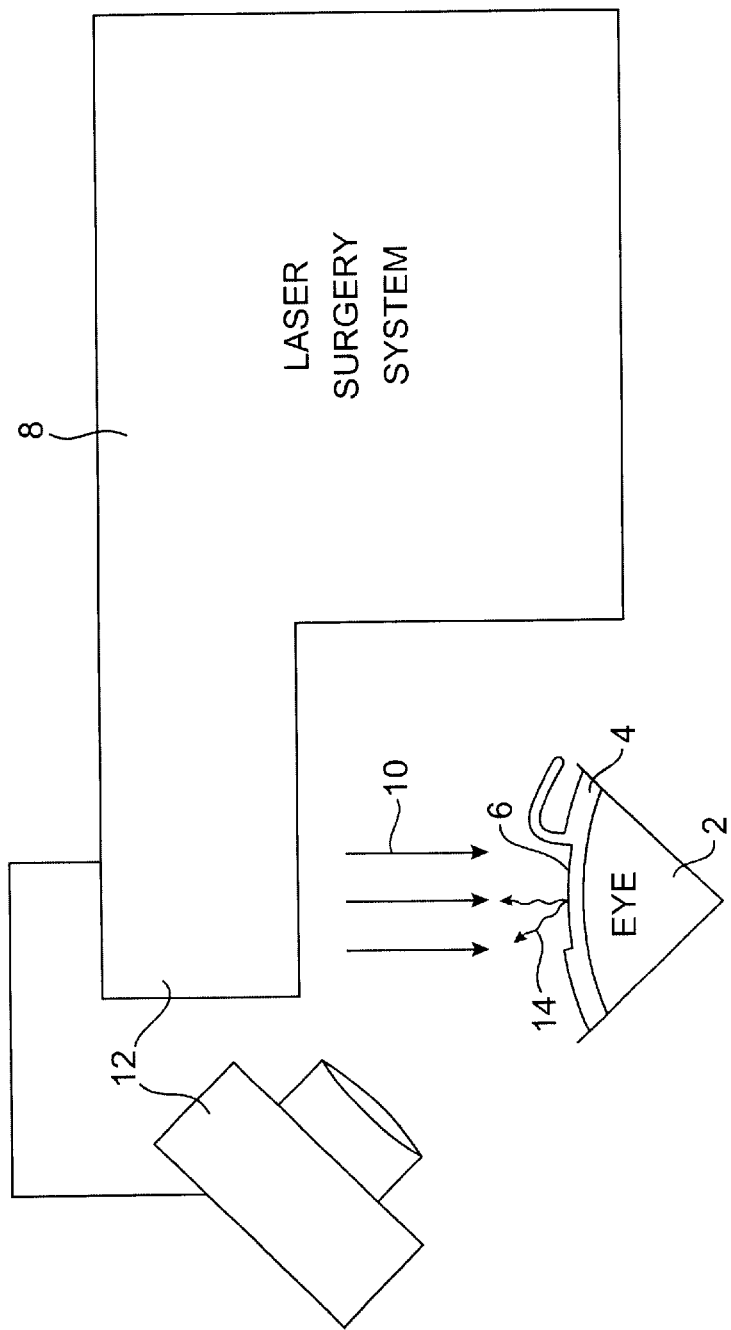
FIG. 1 schematically illustrates a laser system and method for sculpting an eye to a desired shape with a laser beam.

During laser resculpting surgeries an exposed surface 6 of a cornea 4 of an eye 2 is changed as illustrated in FIG. 1. A laser system 8 makes a laser beam 10. The laser beam 10 ablates tissue from the exposed surface 6 of the eye 2. A surface topography system 12 measures the shape of the exposed corneal surface 6 by making a fluorescent light energy 14 with the cornea 4.

Figure 2:
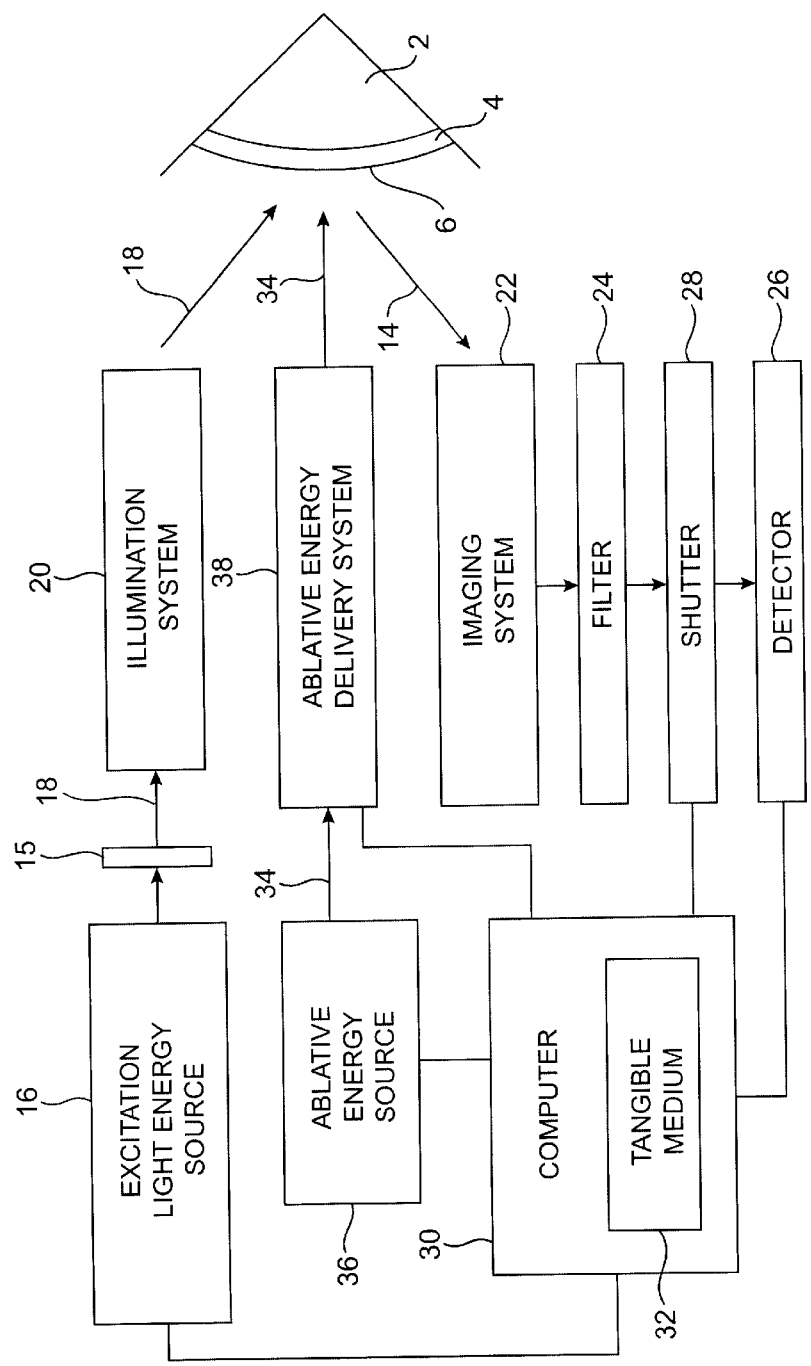
FIG. 2 illustrates a block diagram of the invention.

The functional elements included in the surface topography system 12 are generally illustrated in FIG. 2. A light source 16 makes an excitation light energy 18 that induces a fluorescent light energy from the eye 2. The system 12 may include a filter 15 for selecting an excitation light energy having an appropriate wavelength from a light energy made by the light source 16. The light source 16 is any suitable light source making an appropriate excitation light energy. An appropriate excitation light energy induces a fluorescent light energy when a tissue absorbs the excitation light energy and emits a fluorescent light energy. Generally, the fluorescent light energy will have a different wavelength than the excitation light energy.

Although many wavelengths of excitation light energy can be used, the wavelength of the excitation light energy is preferably from about 150 to 400 nm, and more preferably from about 190 to 220 nm, for measuring an exposed tissue surface. Although many wavelengths of fluorescent light energy can be measured, the measured fluorescent light energy is preferably from about 250 to 500 nm, and more preferably from about 300 to 450 nm. Examples of suitable light sources to provide this excitation energy include visible, ultraviolet and infrared lasers, deuterium lamps, arc lamps, and the like.

When measuring the surface topography of the exposed surface 6 of the eye 2, the light source 16 preferably makes an excitation light energy having wavelengths from about 190 to 220 nm, which is strongly absorbed by the cornea 4. Most of the light energy is absorbed within about a one $\mu$m tissue depth, so that a fluorescent tissue layer that emits the fluorescent light energy is also limited to about a one $\mu$m tissue depth. This limiting of the fluorescent tissue layer to about a one $\mu$m depth permits very accurate measurement of the anterior corneal surface topography with resolution of about one $\mu$m.

Alternatively, the excitation light energy may be weakly absorbed by the eye to permit penetration of the light energy to deeper tissue structures of the eye such as the lens. This deeper penetration of the excitation light energy permits the measurement of the shape of a deeper tissue structure such as the posterior surface of the cornea and the surfaces of the crystalline lens of an eye. An example of a suitable light energy for the measurement of a deeper tissue structure of the eye is light energy having a wavelength between about 300 and 400 nm.

In some embodiments, a projection system 20 projects the excitation light energy 18 from the light source 16 onto the eye 2 in a controlled irradiance pattern. An imaging system 22 images the fluorescent light 14 emitted by the eye 2. The imaging system 22 images the fluorescent light energy 14 onto a detector 26. The detector 26 is sensitive to the fluorescent light energy 14 and measures an intensity of the fluorescent light energy 14. The detector 26 is preferably a vidicon tube coupled to a CCD (charge coupled device) array, but could be any suitable spatially resolved detector such a CCD array or a CMOS (conducting metal oxide semiconductor) area sensor, a linear array detector or photographic film.

The system 12 may include a shutter 28 that is synchronized with a pulsing of the light source 16. Shutter 28 opens to allow fluorescent light energy to be detected by the detector 26. The shutter 28 is preferably an electronic shutter, but may be a mechanical shutter. The opening of shutter 46 is synchronized with a pulsing of the light source 16 to increase the signal-to-noise ratio of the measured fluorescent light energy. System 12 may also include a filter 24 for selecting a fluorescent light energy emitted by the eye 2, and for excluding light from other light sources, such as visible lights used with operating microscopes.

In some embodiments, a processor or computer 30 is coupled to the detector 26, the light source 16 and shutter 28. The computer 30 includes a tangible medium 32. The computer 30 calculates a shape of the eye 2 from the intensity of the fluorescent light energy 14 measured by the detector 26.

The invention may include an ablative energy source 26 for making an ablative energy 34, and an ablative energy delivery system 28. Suitable ablative energy sources include excimer, free electron and solid state lasers emitting ultraviolet light and pulsed infrared lasers. A suitable energy source emits energy that is strongly absorbed by the tissue so that most of the energy is absorbed within about a 1 $\mu$m depth into the tissue. An example of a suitable excimer laser is an argon fluoride excimer laser emitting ultraviolet light having a wavelength of 193 nm. An example of a suitable solid state laser is a laser producing an ultraviolet light energy having a wavelength of 213 nm that is generated by a fifth harmonic from a yittrium aluminum garnet (YAG) laser having a fundamental wavelength of 1064 nm. An example of a suitable infrared laser is a erbium YAG laser producing light energy having a wavelength of 2.9 microns. The following patents describe suitable ablative energy sources and the full disclosures of these patents are herein incorporated by reference: U.S. Pat. No. 5,782,822 (by Telfair) and U.S. Pat. No. 5,520,679 (by Lin). Ablative energy source 26 and ablative energy delivery system 28 are coupled to the computer 30. Ablative energy delivery system 28 and computer 30 control the exposure of the eye 2 to the ablative energy to sculpt the eye 2 to a desired shape.

Some of the elements shown in FIG. 2 may be combined. For example, elements used in the projection system 22 may be used in the imaging system 30. Also, the ablative light source 26 may also function as a light source 16 for making an excitation light energy 18, and the ablative light energy 34 may function as the excitation light energy 18. In some embodiments, the ablative energy delivery system 28 may comprise some or all of the elements of projection system 20.

Figure 3:
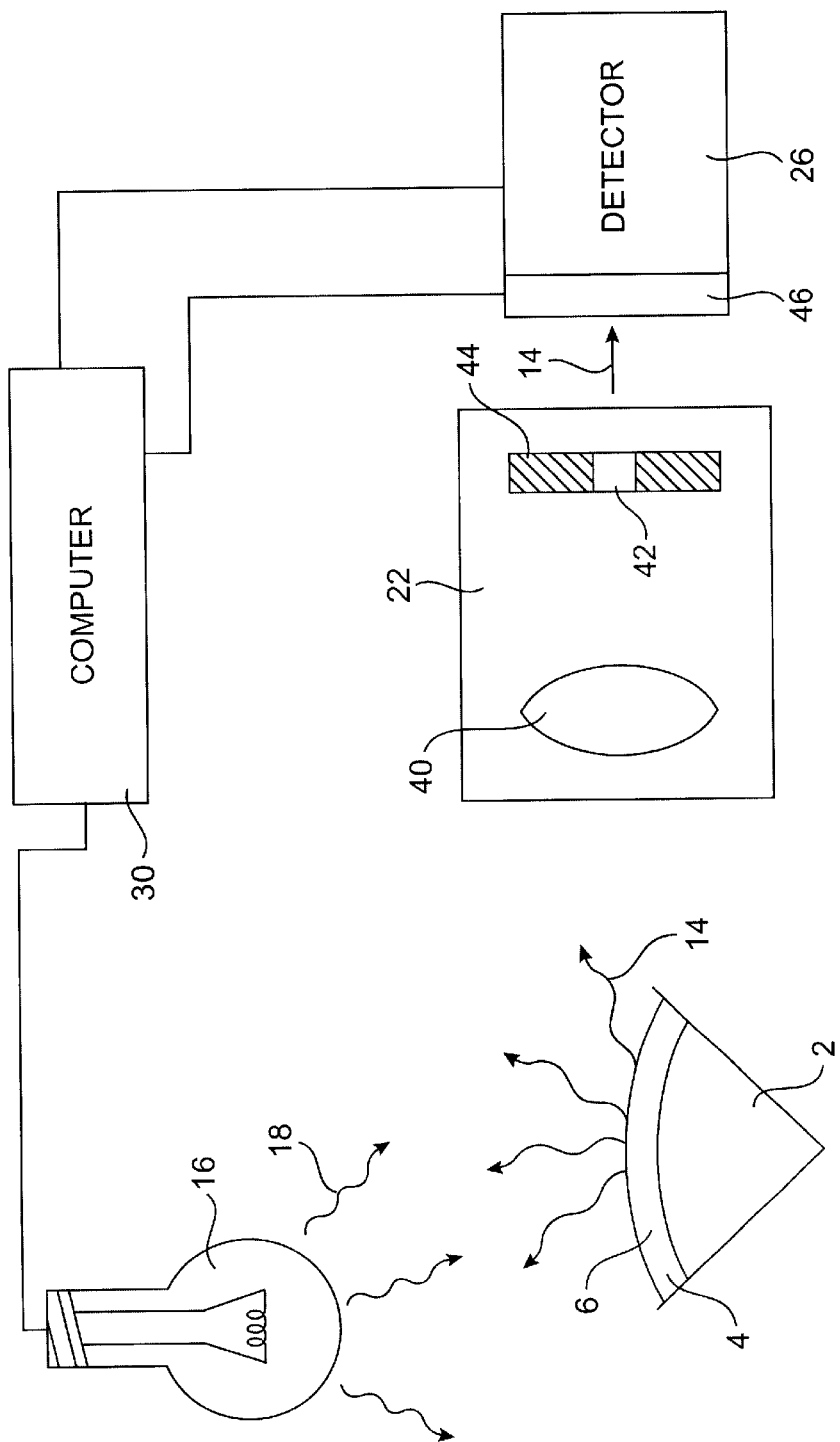
FIG. 3 schematically illustrates an embodiment of the invention incorporating a side view camera.

An embodiment of the invention is shown in FIG. 3. A light source 16 makes an excitation light energy 18. The excitation light energy 18 is absorbed by the corneal tissue 4, and induces the tissue to make a fluorescent light energy 14. The imaging system 22 images the fluorescent light energy 14 onto a detector 26. The imaging system 22 includes a lens 40 and an aperture 42 for restricting the passage of the fluorescent light energy to increase the depth of field of the imaging system 22. The aperture 42 comprises a non-transmitting material 44. The aperture 42 is preferably positioned at the focal length of the lens 40 to make a telecentric imaging system. However, the aperture 42 may be positioned at other locations near the lens 40. A computer 30 is coupled to the light source 16, the shutter 46 and the detector 26. The computer 30 calculates the shape of an exposed surface 6 from an intensity of the fluorescent light energy 14 measured by the detector 26.

Figure 4:
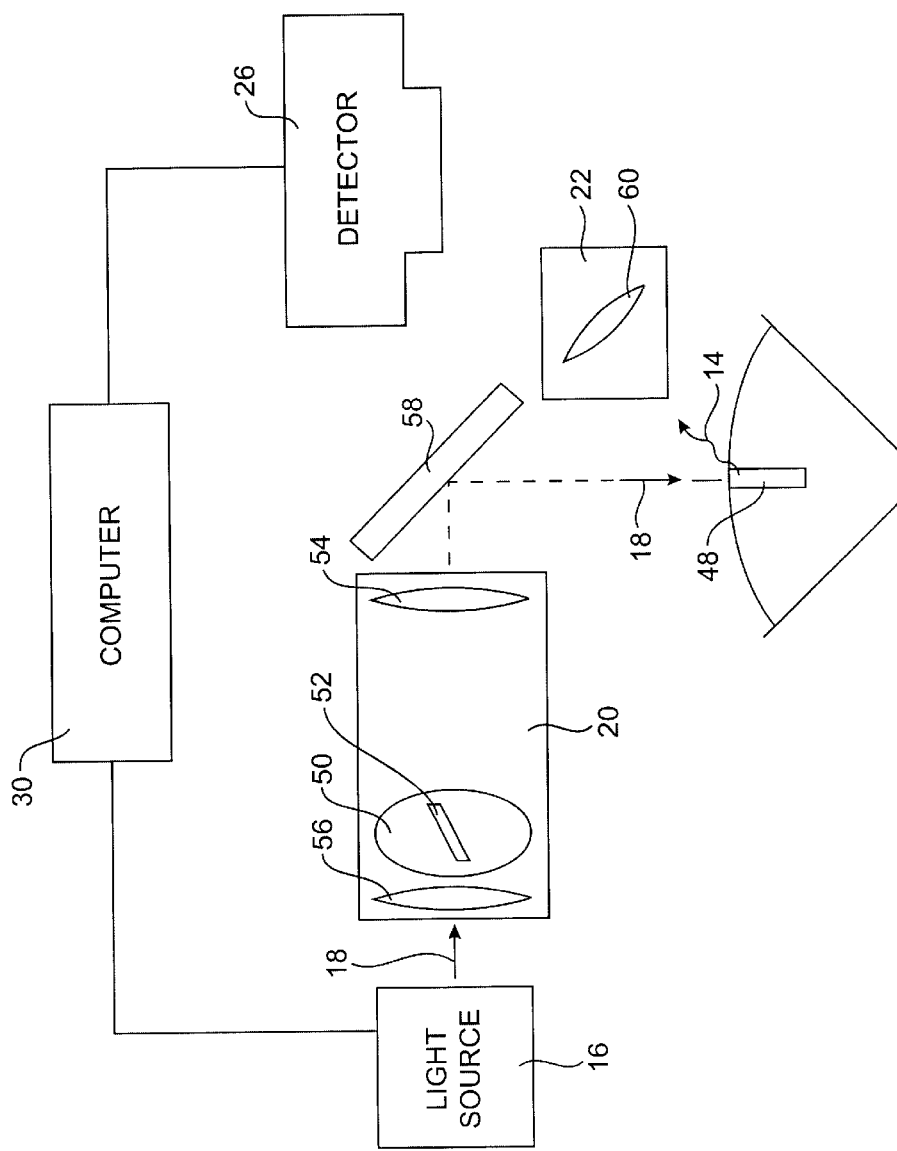
FIG. 4 illustrates an embodiment of the invention incorporating a projected slit and a Scheimpflug imaging system.

An alternate embodiment employing a controlled irradiance pattern comprising a projected slit of light energy is illustrated in FIG. 4. A technique for measuring the surfaces of the cornea by illuminating the eye with a slit and imaging the eye onto a vidicon tube is described in U.S. Pat. No. 4,019,813, the entire disclosure of which is herein incorporated by reference. Light source 16 makes an excitation light energy 18. The corneal tissue 4 absorbs the excitation light energy 18 to make a fluorescent light energy 14. The projection system 20 projects the excitation light energy 18 onto the cornea in a controlled irradiance pattern 48 comprising a slit. The excitation light energy 18 passes through an aperture formed as a slit 52 in a non-transmitting material 50. An imaging lens 54 forms an image of the light passing through the slit 52 near the eye 2. A field lens 56 positioned adjacent to the slit aperture increases the depth of field of the image of the slit aperture formed near the eye 2. A mirror 58 reflects the projected light energy onto the eye 2. The eye 2 absorbs the projected excitation light energy to make a fluorescent light energy 14. The imaging system 22 images the fluorescent light energy 14 emitted by the eye 2 onto a detector 26. The imaging system 22 is a scheimpflug imaging system and includes a lens 60 for imaging the eye 2 onto the detector 26. This imaging technique permits different layers of the eye 2 to be imaged onto the detector 26.

Figure 5:
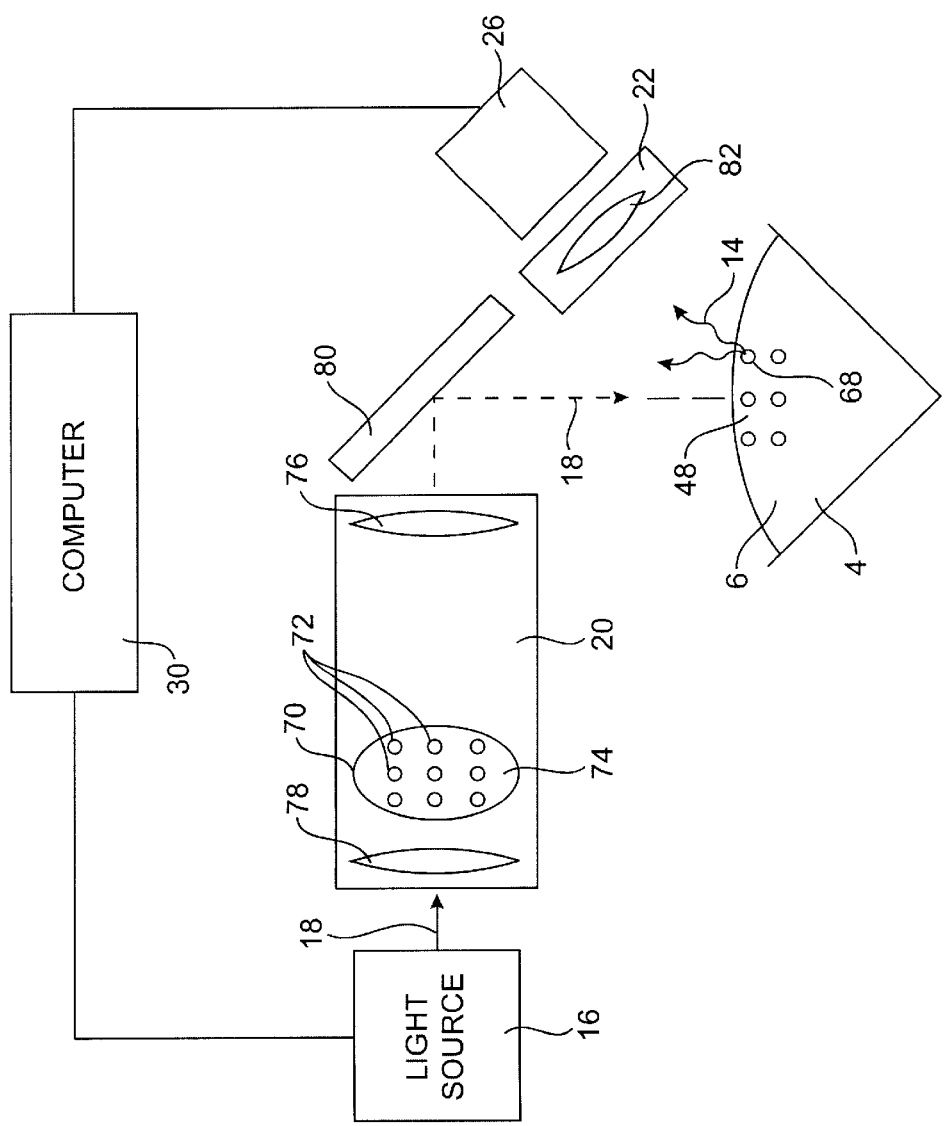
FIG. 5 illustrates an embodiment of the invention incorporating a triangulation technique.

Another embodiment employing controlled irradiance pattern comprising a projected grid is illustrated in FIG. 5. Techniques for measuring the surface topography of a cornea with a projected grid are described in U.S. Pat. Nos. 3,169,459; 4,761,071; 4,995,716 and 5,159,361; the full disclosures of these patents are herein incorporated by reference. A light source 16 makes an excitation light energy 18. A projection system 20 projects a controlled irradiance pattern 48 of the excitation light energy 18 onto the eye. The controlled irradiance pattern here comprises a grid 58. The grid 58 preferably comprises a rectilinear array of focal points of an excitation light energy 18. Alternatively, the grid 58 may be a circular array of focal points of an excitation light energy. In other embodiments, the grid may include a rectilinear or circular array of lines of an excitation light energy 18. irradiance pattern of the excitation light energy is shaped into a grid by passing the excitation light energy through a grid element 70 comprising an array of small circular apertures 72 formed in a non-transmitting material 74. An imaging lens 76 forms an image the grid element 70 near the cornea 4.

A field lens 78 is positioned near the grid element 70. The field lens 78 increases the depth of field of the image of the grid element 70 formed near the cornea 4. A mirror 80 reflects the projected image of the grid element 70 toward the cornea 4. The cornea 4 absorbs the excitation light energy 18 and emits the fluorescent light energy 14. The imaging system 22 images the fluorescent light energy onto a detector 26. The imaging system 22 comprises an imaging lens 82.

The positions of the features of the grid imaged on the detector are calculated by computer 30. The surface elevations of the features of the grid projected onto the eye are calculated by triangulating the fluorescent light rays for the imaged features of the grid with the excitation light rays for the projected features of the grid. The topography of the surface of the eye corresponds to the elevation of the features of the grid projected onto the eye. Alternatively, the surface elevation of the features of the projected grid may be determined by stereo images of the grid from two imaging systems and detectors viewing the projected grid at different angles.

Figure 6:
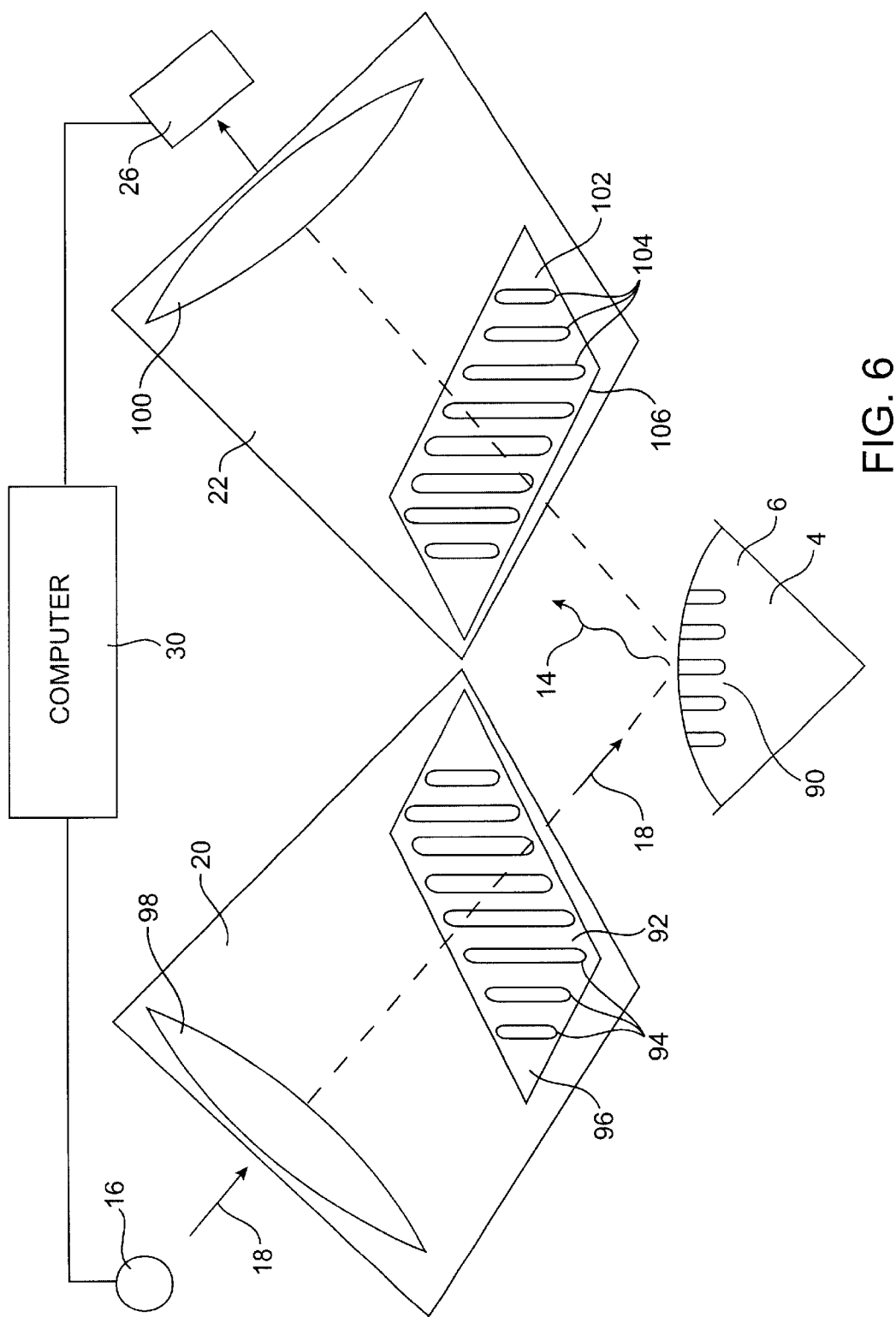
FIG. 6 illustrates an embodiment of the invention incorporating a moire technique.

A further embodiment includes using tissue fluorescence to make moire fringe patterns to measure surface topography as illustrated in FIG. 6. With this technique overlapping patterns create a fringe pattern. The fringe pattern is used to derive a topography of an exposed surface. A controlled irradiance pattern comprising an excitation light energy 18 is projected onto a cornea 4 of an eye 2. Viewing a projected light pattern through an aperture pattern preferably makes the overlapping patterns as illustrated in FIG. 6. Alternatively, overlapping a pair of light patterns makes a fringe pattern as described in U.S. Pat. No. 5,406,342, the full disclosure of which is herein incorporated by reference.

The overlapping patterns are preferably an array of straight lines, but may be an array of circular lines or an array of small areas such as quasi-rectangular areas made by passing light energy through a screen. Alternatively, the small overlapping areas may be circular areas.

An embodiment that employs a light pattern overlapping with an aperture pattern is illustrated in FIG. 6. Light source 16 makes an excitation light energy 18. An illumination system 20 casts an array of straight lines 90 of excitation light energy 18 onto an exposed surface 6 of cornea 4. The array of straight lines 90 are formed by passing the excitation light energy 18 through an array 92 of apertures formed as slits 94 in a non-transmitting material 96. A lens 98 collimates the excitation light energy 18 emitted by the light source 16. The collimated excitation light energy 18 passes through the slits to form the array of straight lines 90 on the cornea 4.

An imaging system 22 images the fluorescent light energy emitted from the cornea 4 onto a detector 26. The imaging system 22 includes an imaging lens 100. The imaging lens 100 forms an image of an image of the cornea 4 on the detector 26. An array 102 of apertures formed as slits 104 in a non-transmitting material 106 is positioned between the detector 26 and the cornea 4. Viewing the array of straight lines 90 on the cornea 4 through the array 102 creates a moire fringe pattern at the detector 26. A person of ordinary skill in the art can derive a surface topography from a moire fringe pattern.

Alternatively, a single array of apertures formed in a non-transmitting material may be positioned adjacent to the eye, and the excitation and fluorescent light energy passed through the array to make a moire fringe pattern. The following U.S. Patents disclose techniques for measuring surface topography with moire fringe patterns and are herein entirely incorporated by reference: U.S. Pat. Nos. 4,692,003; 5,406,342; and 4,459,027.

Figure 7:
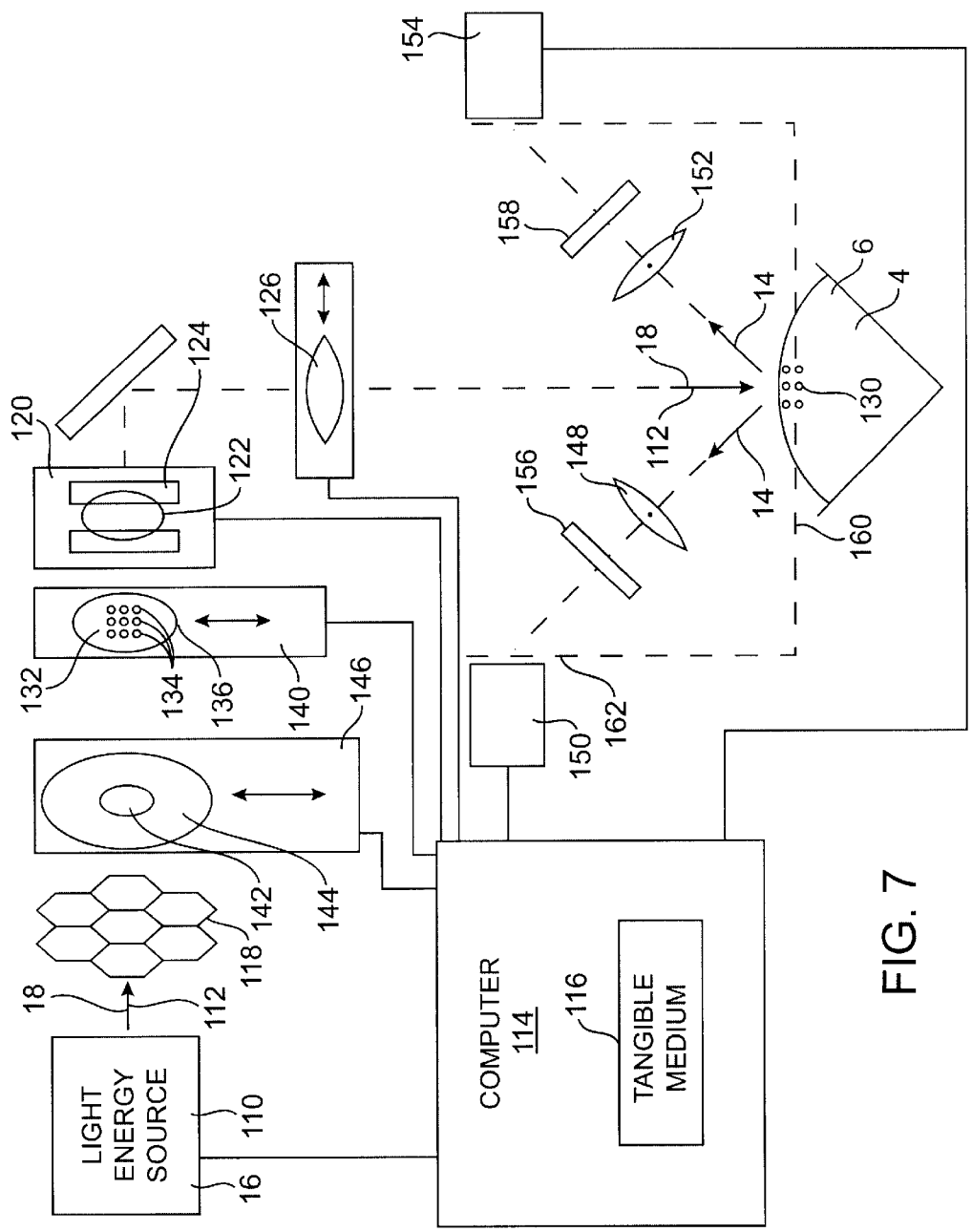
FIG. 7 illustrates an embodiment of the invention integrating an ablative laser with a stereo imaging system.

An exemplary apparatus embodiment integrating a fluorescence topography system with an ablative laser system is illustrated in FIG. 7. The ablative laser system is preferably a Star S2 excimer laser system available from VISX, Incorporated of Santa Clara, Calif. An ablative light energy source 110 makes an ablative light energy 112. The ablative light energy source is an excimer laser producing 193 nm light energy. The excitation light energy 18 is also 193 nm light energy. A computer 114 comprises a tangible medium 116. The computer 114 controls the laser system and the exposure of ablative energy on a surface of a cornea 4 of an eye 2 to correct a refractive error of eye 2. The laser system includes a spatial integrator 118 for making a uniform laser beam energy distribution at the eye 2. The spatial integrator 118 overlaps the different portions of the laser beam at the plane of the eye 2 to make a uniform laser beam as described in U.S. Pat. No. 5,646,791, and the full disclosure of this patent is herein incorporated by reference.

The system also includes a beam shape module 120 for area profiling the ablative laser beam 112. The beam shaping module 120 comprises an adjustable iris diaphragm 122 for controlling a diameter across the laser beam on the eye and a pair of blades having an adjustable width between the blades for controlling a rectangular width across the laser beam as described in U.S. Pat. No. 5,713,892. The laser system also includes a moveable lens for scanning an image of the area profiled laser beam over the eye as described in U.S. patent application Ser. No. 08/968,380.

To measure a shape of an exposed surface 6 of a cornea 4, a grid 130 of focal points of excitation light energy illuminate an exposed surface 6 of a cornea 4. The excitation light energy 18 passes through an array 132 of circular apertures 134 formed in a non-transmitting material 136. The imaging lens 126 forms an image of the light passing through the circular apertures near the exposed surface 6 of a cornea 4 to form the grid 130.

A mechanical actuator 140 controls the position of the array 132 and is controlled by a computer 114. The array 132 is selectively inserted into the laser beam path by the mechanical actuator 140 when a shape of the eye 2 is measured. The intensity of the ablative light energy source 110 is adjusted to make an energy density of a laser beam pulse to be below a threshold of ablation at an exposed surface 6 of a cornea 4.

An aperture 142 formed in a non-transmitting material 144 is inserted into the laser beam path to increase a depth of field of the image of the array 132 near the cornea 4. An actuator 146 controls a position of the aperture 142 and is under control of a computer 114.

A pair of imaging lenses 148 and 152 form a pair of stereo images at detectors 150 and 154 when the ablative light energy source pulses to make an excitation light energy. Imaging lens 148 and detector 150 are arranged in a scheimpflug configuration. A plane 160 parallel to a front surface of the eye is imaged as a plane 162 at the detector 150. The plane 162 is perpendicular to the plane 160 and a front surface of the eye. Imaging lens 152 and detector 154 are arranged in a similar scheimpflug configuration. The grid 130 is projected near and approximately coplanar with the plane 160, and the anterior surface 6 of the cornea 4 is positioned near the plane 160. This scheimpflug configuration minimizes distortion and blur in the image of grid 130 formed at detectors 150 and 154 and increases the accuracy of the measured surface elevation.

Detectors 150 and 154 comprise electronic shutters that open when the ablative light energy source produces the laser beam pulse. A pair of optical filters 156 and 158 selectively pass a fluorescent light energy 14 and block an excitation light energy 18 and a visible light energy for viewing the eye 2 with an operating microscope. The computer 114 calculates the exposed surface topography from the stereo images. Relevant techniques are described in U.S. Pat. Nos. 4,669,466 and 4,665,913, the full disclosure of which are incorporated herein by reference.

The topography of the exposed surface 6 is measured before and after an ablation of the exposed surface 6. A change in the measured topography of the exposed surface 6 is calculated and is the measured laser ablation profile. The measured laser ablation profile is compared to an intended laser ablation profile. A difference between the intended and measured laser ablation profiles is calculated, and additional tissue is ablated to form the measured ablation profile to the intended laser ablation profile.

Figure 8:
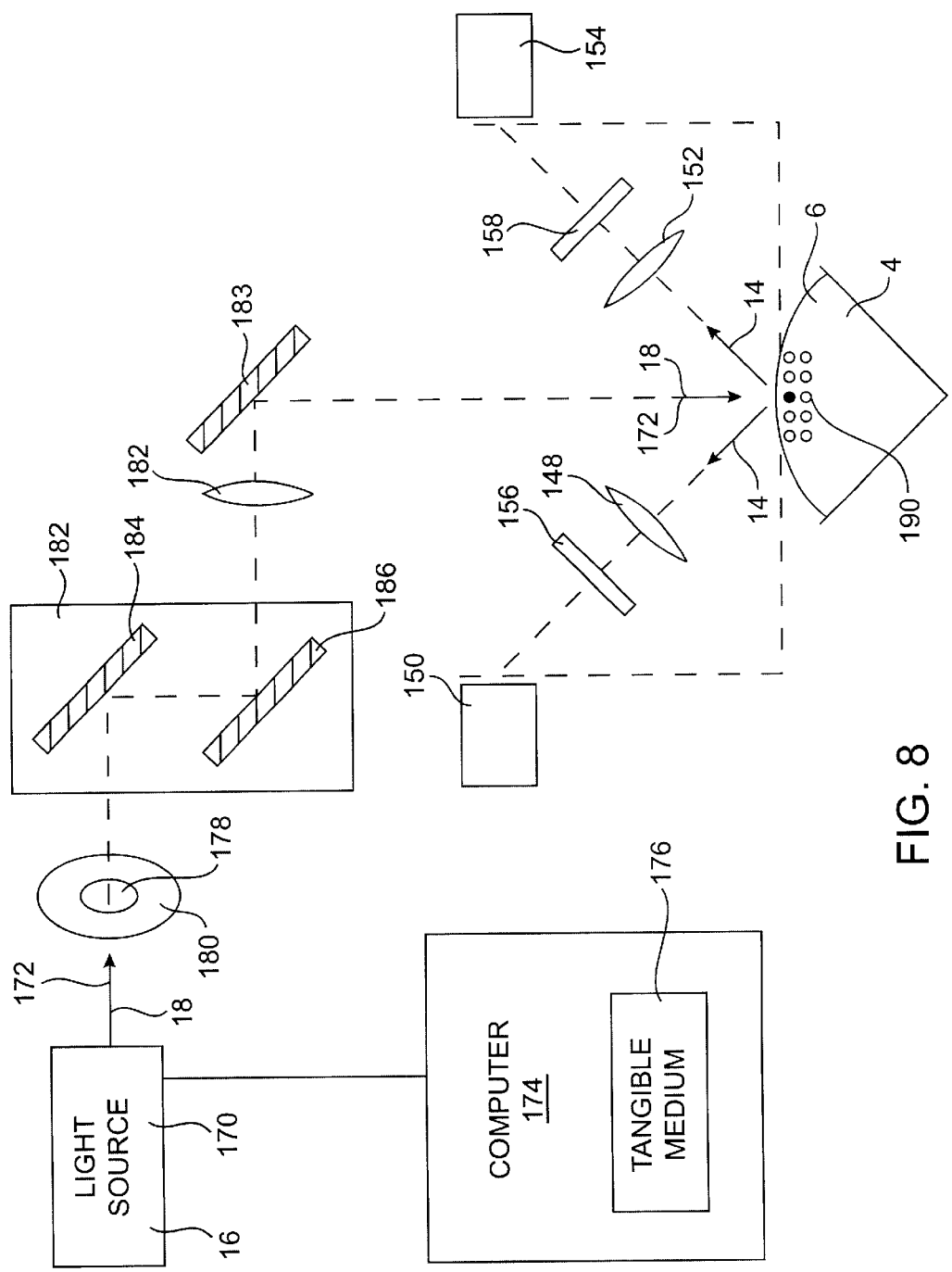
FIG. 8 illustrates an embodiment of the invention integrating a scanning ablative laser with a stereo imaging system.

Another exemplary embodiment integrating a fluorescence topography system with a scanning ablative laser system is illustrated in FIG. 8. An ablative light energy source 170 makes an ablative light energy 172. The ablative light energy source is a frequency quintupled pulsed YAG laser producing 213 nm light energy. The excitation light energy 18 is also 213 nm light energy. A computer 174 comprises a tangible medium 176. The computer 174 controls the laser system and the exposure of ablative light energy on a surface of a cornea 4 of an eye 2 to correct a refractive error of eye 2. The system also includes an aperture 178 formed in an non-transmitting material 180 and a lens 182 for shaping and focusing the laser beam at an exposed surface 6 of the cornea 4.

The system also includes a scanning mechanism 182 for deflecting the laser beam over the exposed surface 6. The scanning mechanism 182 comprises a pair of rotating mirrors 184 and 186 as scanning elements. Alternatively, the scanning mechanism may comprise moving lenses and prisms as scanning elements.

A computer 174 is electronically coupled to ablative energy source 170 and scanning mechanism 182. The computer 174 controls the position and energy of the ablative light energy pulses, defining the pattern of ablative energy delivered to the exposed surface 6 of the cornea 4. A pulse of the ablative light energy 172 removes tissue and also acts as a pulse of an excitation light energy 18 to induce a fluorescent light energy 14 from the tissue. A position of the tissue removing pulse of ablative light energy is measured by stereo images of the fluorescent light energy emitted by the tissue as described above. The topography of the exposed surface is derived from a succession of sequential ablative light energy pulses.

The succession of tissue removing ablative light energy pulses may be delivered in a predetermined pattern to form a grid 190 on the exposed surface 6. Alternatively, the energy of the ablative light energy may be adjusted so that the succession of ablative light energy pulses does not remove tissue and has an energy level below a threshold of ablation of the cornea 4. The topography of the exposed surface 6 corresponds to the positions of the pulses of ablative light energy comprised by the grid 190.

Figure 9:
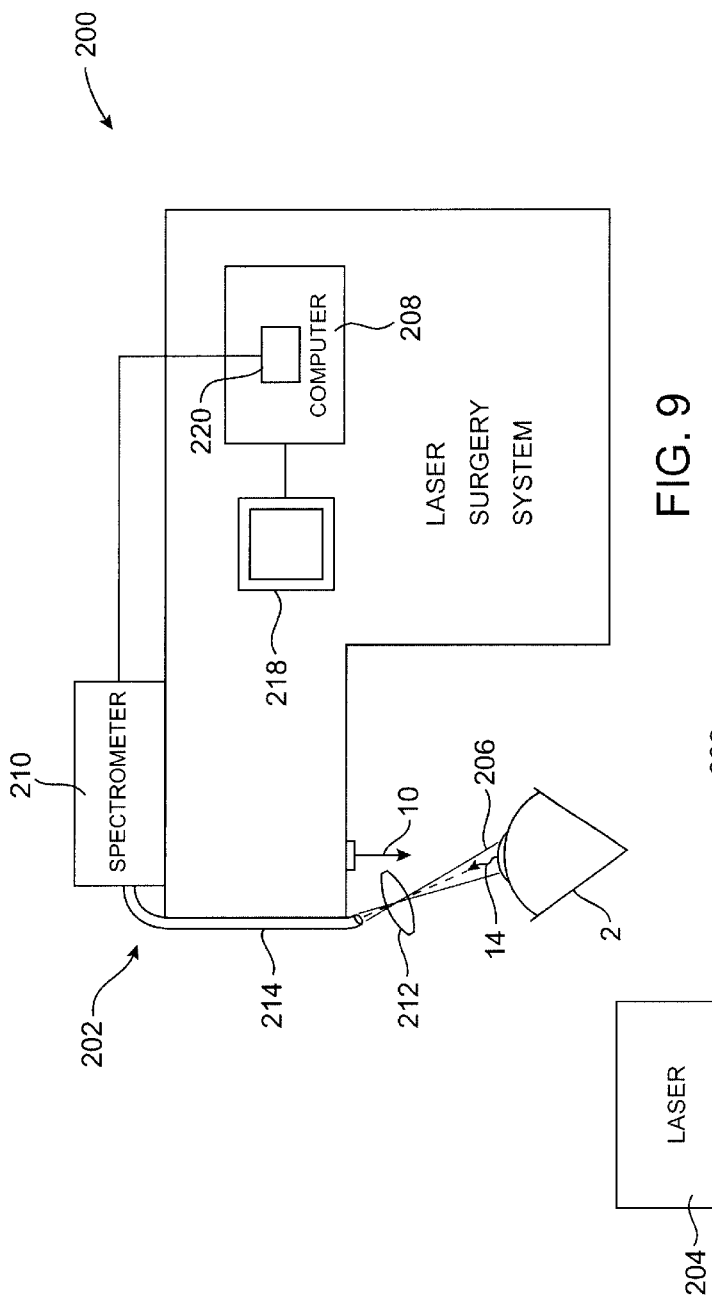
FIG. 9 schematically illustrates a laser system and method for sculpting an eye to a desired shape while sensing and compensating for hydration of the corneal tissue.

Referring now to FIG. 9, a laser surgery apparatus 200 generally includes the resculpting components described above, and also includes a hydration measurement and compensation system 202. Hydration system 202 again uses the ablative laser energy 10 to induce fluorescence in corneal tissue of eye 2, and may also share many of the components of the topography measurement system described hereinabove.

Figure 10:
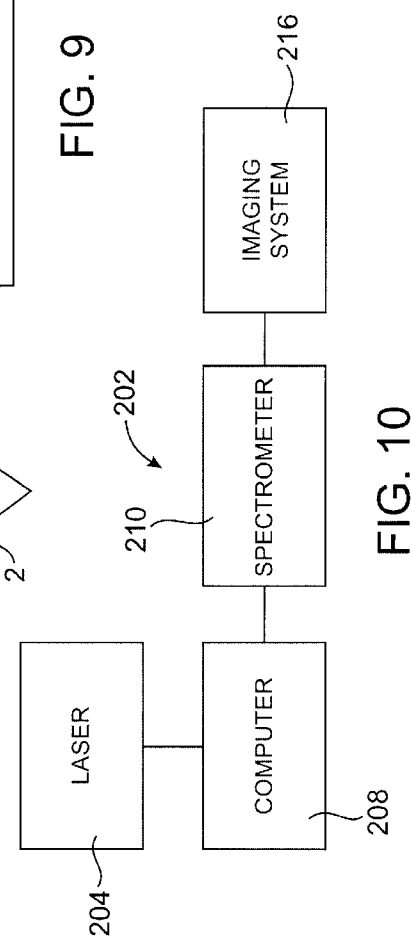
FIG. 10 is a block diagram of the hydration sensing apparatus of the system of FIG. 9.

Referring now to both FIG. 9 and 10, hydration system 202 will generally comprise an excitation light source 204 directing laser energy 10 toward a target region 206 on an exposed surface of eye 2. This excitation energy incites the corneal tissue to fluoresce, and may optionally also ablate a portion of the corneal tissue.

In general terms, hydration system 202 includes a sensor which generates a signal indicating fluorescent light energy 14 from eye 2 induced by the excitation energy. A processor 208 calculates the hydration of the corneal tissue using the fluorescent light signal from the sensor. More specifically, the sensor will typically comprise a spectrometer 210. Imaging optics, here comprising an imaging lens system 212 and a fiber optic cable 214 direct fluorescent light energy 14 from target region 206 of eye 2 to the spectrometer.

Generally, the fluorescent light sensor will measure an intensity of fluorescent light 14 from eye 2. Optionally, imaging system 216 may direct the fluorescent light energy to a bulk sensor arrangement to determined the overall hydration of the excited tissue. Alternatively, the imaging system may image the fluorescing tissue surface onto a spatially resolved detector for measuring variations in hydration across the excited tissue, and/or across the target region. Hence, computer 208 may modify the ablative energy pattern delivered from laser 208 to eye 2 so as to compensate for variations in the ablation rate due to the hydration of the tissue, either locally or globally.

In an exemplary spatially resolved detection system, lens 212 images the fluorescing tissue surface onto a second generation image intensifier tube, which may be gated or synchronized to the laser pulse, and which is coupled to a CCD array. Computer 208 compares the fluorescing energy to the laser energy, and adjusts the laser exposure using the measured fluorescence. The spatial distribution of laser energy within the ablative energy pattern is adjusted based on the spatial intensity variation of the imaged fluorescence.

Corneal stroma ablated with a 6 mm uniform energy laser beam will not always create a uniform fluorescence pattern. The central portion of the ablating stroma fluoresces more strongly, possibly because of its increased water content. This increased water content of the central portion of a large area ablation may also lead to under ablation of this central region, sometimes called "central islands." Hence, the fluorescence pattern may be used to sense and compensate for the hydration (and hence the under ablation) of the central region of an ablation. Typically, the reduced ablation depth is compensated for by increasing the pulses directed to the central, more highly hydrated region. Such spatially resolved hydration measurements may also be used to correct the ablation shape where the measured hydration distribution deviates from the standard central island hydration distribution. Alternatively, in a very simple arrangement, computer 208 may simply provide a signal to a display 218 indicating that the hydration distribution or total hydration of the tissue is beyond a desired or acceptable range, optionally with no automatic adjustment of the laser system. In fact, display 218 simply comprise a three-color light system indicating, for example, a dry cornea with a red light, a wet cornea with a blue light, and a cornea in a "normal" range (for which no ablation adjustment is needed) with a green light. Some or all of these capabilities may be included when using spectrometer 210 as the fluorescent energy detector.

Figure 11:
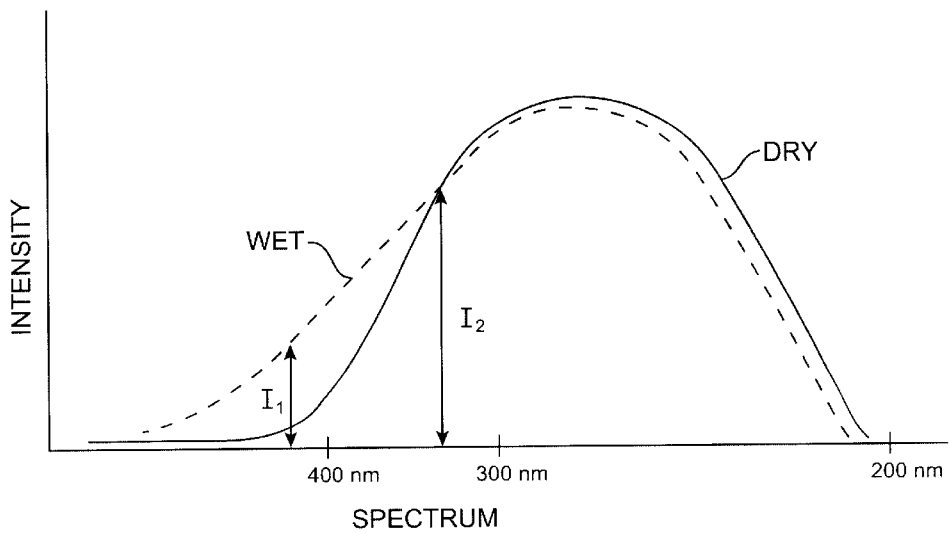
FIG. 11 graphically illustrates a method for calculating hydration as a function of relative intensities of selected wavelengths of the fluorescent light generated by a tissue.

Referring now to FIGS. 9 and 11, computer 208 will generally include a hydration module 220 for calculation of local or global hydration using fluorescent light intensity signals provided from spectrometer 210. Hydration module 220 may comprise hardware, software (generally in the form of a tangible medium, as described above), firmware, or any combination thereof. Hydration module 220 will preferably use an intensity signal from spectrometer 210 indicating an intensity of the fluorescent light energy at a first frequency $I_1$. This first intensity signal will preferably be measured at a wavelength which varies considerably with changes in hydration of the tissue, as can be understood with reference to FIG. 11. Generally, this hydration-sensitive wavelength will be in a range from about 350 to about 450 nm, ideally from about 375 to about 425 nm. It should be understood that the signal will typically measure intensity along some band of wavelengths, rather than at a single theoretical point in the spectrum. The first intensity signal may be normalized using a second intensity signal measured at a reference wavelength $I_2$, with the reference wavelength preferably having an intensity which is substantially insensitive to variations in tissue hydration. Such insensitive frequencies are often found at crossover points along the intensity/spectrum graph for different hydrations. Suitable hydration-insensitive wavelengths may be found in a range from about 250 to about 375 nm, for example, at about 350 nm. The hydration may then be determined empirically as a function of the relative intensities $I_1 \div I_2$. This helps to avoid sensitivity to the various environmental conditions at which the measurements are taken.

In some embodiments the computer may calculate hydration using a correlation of a measured waveform from the eye with a plurality of reference waveforms. Suitable reference waveforms include a spectrum from a dry cornea tissue, and a spectrum from water. Hence, a variety of measurements and calculations are encompassed by the present invention.

Figure 12:
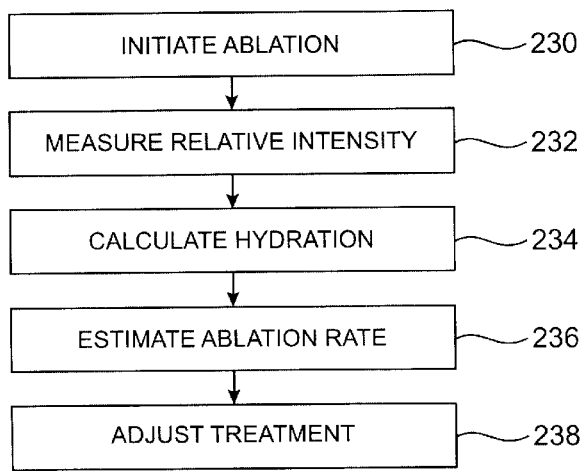
FIG. 12 is a flow chart schematically illustrating a method for compensating for hydration during an ablation procedure.

Referring now to FIG. 12, an exemplary method for performing a hydration compensated photorefractive ablation may be initiated using a predetermined ablation pattern assuming a standard ablation rate in block 230. Ablative laser energy 10 induces fluorescence of the corneal tissue, and the relative intensity of a hydration sensitive light wavelength of the fluorescent light energy 14 is measured relative to the reference wavelength in block 232. Hydration of the fluorescing tissue is then calculated by computer 208 from the relative intensities in block 234, so that the ablation rate can be estimated (again based on empirical ablation data) from the tissue hydration in block 236. The estimated ablation rate may then be used in place of the standard ablation rate assumed when the ablation was initiated, and the treatment adjustment by varying the pattern of ablation energy directed toward the tissue so as to effect the desired change in optical characteristics of eye 2. The change in treatment pattern will often comprise changes in the size, location, and/or number of laser pulses directed toward some or all of the treatment region of the eye. The adjustment may simply comprise varying a diopter power of a standard ablation pattern (for example, programming a laser to ablate to 3.5 diopters instead of 4 diopters for a measured hydration which is less than a standard assumed hydration of the corneal tissue). Alternatively, the algorithm used to calculate a shot pattern so as to effect a desired change in corneal shape may be rerun using locally adjusted estimated ablation rates appropriate for varying hydration across the treatment region.

Still further alternative embodiments of the present invention are possible. For example, a photomultiplier tube and circuitry might be used to measure fluorescent light energy so as to calculate the hydration. Hence, many of the topography measurement components described above might be used for hydration measurements, and/or these hydration measurement components may be used to derive topographic information. Clearly, both the topographic information and hydration information may be used as feedback to modify an ablation procedure.

A variety of alternative specific components may be used within the scope of the present invention. For example, ellipsometry has been developed and used in the semiconductor and optics industries to measure the thickness of thin films. By observing and/or measuring light reflected from a thin transparent film, and more specifically by determining the degree of ellipticity of polarized light, an ellipsometer can measure the film thickness, globally and/or locally. Such techniques could be applied to measure the thickness of a moisture layer on the surface of the cornea. Once again, this surface hydration information might be used to modify an ablation procedure to improve the resculpting of the corneal tissue. Ellipsometers are commercially available from a number of suppliers for specialized applications.

Figure 13A:
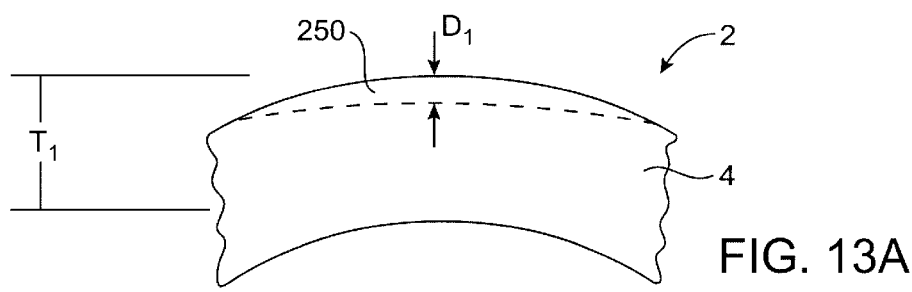
FIGS. 13A and 13B schematically illustrate a method for sculpting a corneal tissue of an eye based at least in part on hydration and/or swelling of the corneal tissue.
Figure 13B:
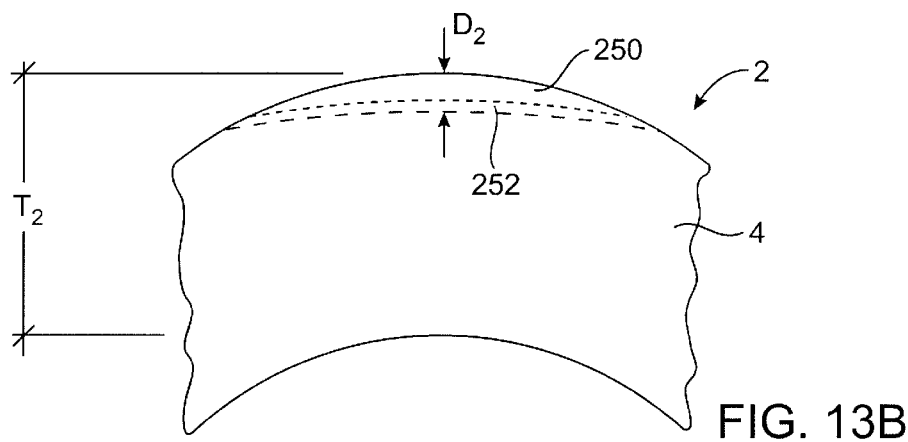

A method of use of the systems described hereinabove can further be understood with reference to FIGS. 13A and 13B. Referring first to FIG. 13A, a variety of methods may be used to measure a desired change in eye 2. Ideally, a wavefront sensor might be used to measure optical properties of the eye so as to define an ablation 250 to effect a desired change in optical properties. Alternative measurements may be made using a variety of topography, tomography, and standard optical measurement and/or diagnostic devices. Ablation 250 here represents the overall change in shape of a corneal tissue 4 (such as a stroma) to effect the desired change in optical properties of the eye.

Unfortunately, the optical measurements made on eye 2 in FIG. 13A will typically be made under quite different conditions than those of the ablation procedure. Specifically, corneal tissue 4 often swells considerably as a result of the standard preparation for and performance of an ablation procedure. Such swelling may be due in part to the addition of therapeutic compounds applied to the eye, incising of the eye to form a flap of corneal tissue which can be displaced to expose the stroma for ablation, and the like. Regardless, an eye 2 having an initial corneal thickness $T_1$ of corneal tissue 4 will typically swell significantly to an enhanced corneal thickness $T_2$ as schematically illustrated in FIG. 13B.

Regardless of the source of swelling of the eye (which may result from the use of a microkeratome, therapeutic compounds applied to the eye, or the like), a modified overall ablation 252 can be applied to the eye to achieve the desired changes in optical properties. Basically, as the additional fluid content of corneal tissue 4 will increase the local tissue thickness and absorb energy during ablation, a nominally sufficient ablation 250 will leave eye 2 undercorrected once the swelling subsides. For example, ablation 250 may be intended to correct a −4 D myopia using a 52 μm ablation depth $D_1$ within an ablation diameter of about 6 mm. Ablation 250 may provide the desired optical change when corneal tissue 4 has an initial and/or normal thickness $T_1$ of about 500 μm. However, the actual change in optical properties of the eye may be insufficient if the ablation takes place after corneal tissue 4 swells to a thickness $T_2$ of about 750 μm.

To provide the desired change in optical property despite the enhanced hydration of eye 2, a hydration-adjusted ablation 252 having a depth $D_2$ of about 78 μm might be used. The hydration-adjusted ablation 252 may have a shape similar to ablation 250, with an overall depth increased proportionally for the increase in tissue thickness. This increase in tissue thickness may be sensed using any of the corneal hydration sensing systems described hereinabove. Typical normal hydration of corneal tissue is about 80%, and tissue thickness may increase proportionally with increasing hydration, so that the adjusted ablation depth may be determined directly from the hydration measurements. As more long-term ablation results are available together with associated hydration measurements made using these systems at the time of the ablation, the correlation between enhanced ablation depth and hydration may be refined.

While the exemplary embodiments have been described in some detail, for clarity of understanding and by way of example, a variety of adaptations, changes, and modifications will be obvious to those of skill in the art. Hence, the scope of the present invention is limited solely by the appended claims.

What is claimed is:

1. A system for measuring hydration of a corneal tissue of an eye, the system comprising:
   a light source directing an excitation light toward the corneal tissue so that the corneal tissue generates fluorescent light, the fluorescent light varying in response to corneal tissue hydration increasing from a normal hydration to an increased hydration;
   a fluorescent light sensor in an optical path of the fluorescent light from the tissue, the sensor generating a signal indicating the fluorescent light; and
   a processor coupled to the sensor, the processor generating a hydration signal indicating the increased hydration of the tissue from the fluorescent light signal.

2. The system of claim 1, further comprising an output device coupled to the processor, the output showing a display in response to the hydration signal.

3. The system of claim 1, wherein the sensor comprises a spectrometer, and further comprising imaging optics directing the fluorescent light along the optical path from the tissue to the spectrometer, the imaging optics forming an image of a target area of the tissue adjacent a detector surface of the spectrometer.

4. The system, of claim 1, further comprising an ablation energy delivery system coupled to the processor, the excitation light comprising an ablative light energy, the delivery system directing the ablative energy toward the corneal tissue, the ablative energy from the delivery system varying in response to the hydration signal.

5. The system of claim 4, wherein the delivery system comprises an optical delivery system transmitting photoablative laser energy toward the corneal tissue so as to selectively alter an optical characteristic of the eye.

6. The system of claim 5, wherein the processor varies a quantity of change in the optical characteristic of the eye in response to the hydration signal.

7. The system of claim 1, wherein an intensity of the fluorescent spectrum of the tissue varies with the hydration, and wherein the signal indicates an intensity of the fluorescent light at a first frequency.

8. The system of claim 7 wherein the processor normalizes the signal using an intensity of the fluorescent light at a second frequency.

9. The system of claim 8, wherein the intensity of the fluorescent light at the second frequency is less sensitive to hydration than the intensity of the fluorescent light at the first frequency.

10. In an apparatus for resculpting a corneal tissue of an eye, the apparatus directing a pattern of light energy from a laser under direction of a processor to effect a desired change in an optical characteristic of the eye, a system comprising:
    a sensor coupled to the processor, the sensor measuring hydration and generating a signal indicating the measured hydration of the corneal tissue; and
    an adjustment module of the processor, the module varying the pattern in response to the measured hydration signal from the sensor.

11. The apparatus of claim 10, wherein the signal varies in response to a thickness of a film of fluid covering a surface of the corneal tissue, the sensor comprising an ellipsometer.

12. A method for measuring hydration-induced swelling of a corneal tissue, the method comprising:
    directing an excitation light toward the tissue so that the tissue generates fluorescent light that varies with changes in response to changes in hydration of the tissue;
    sensing the fluorescent light;
    calculating the hydration of the tissue using the sensed fluorescent light; and
    determining the swelling of the tissue in response to the calculated hydration.

13. The compensation method of claim 12, wherein the excitation light comprises the laser energy.

14. The compensation method of claim 12 wherein the sensing step comprises measuring a thickness of a fluid film on a surface of the eye by ellipsometry.

15. In a procedure for resculpting a corneal tissue of an eye by selectively directing a pattern of laser energy toward the eye to effect a predetermined change in an optical characteristic of the eye, a compensation method comprising:
    sensing a hydration of the tissue; and
    adjusting the pattern of laser energy in response to the sensed hydration.

16. The compensation method of claim 15, wherein the hydration sensing step comprises:
    directing an excitation light toward the tissue so that the tissue generates fluorescent light;
    measuring an intensity of the fluorescent light at a first frequency relative to a second frequency;
    calculating hydration of the tissue using the measured relative intensity.

17. The compensation method of claim 15, further comprising estimating ablation rate for the calculated hydration, wherein the pattern adjusting step varies the pattern in response to the estimated ablation rate.

18. A method for sculpting of a corneal tissue of an eye to effect a desired change in an optical property of the eye, the method comprising:
    sensing hydration of the corneal tissue;
    determining a desired change in shape of the eye in response to the hydration and the desired change in optical property; and
    planning a pattern of laser energy to direct toward the corneal tissue to effect the determined change in shape.

19. The method of claim 18, the desired change in optical quality determined while the eye has a first hydration, wherein the eye swells and the hydration increases from the first hydration to a second hydration, and wherein the desired change in shape is determined using the second hydration.

20. The method of claim 19, wherein the hydration increases and the corneal tissue swells in response to at least one member selected from the group consisting of a therapeutic compound applied to the eye and incising of the eye to expose a tissue for ablation.

21. The method of claim 19, further comprising increasing a total depth of corneal tissue removed from the eye to compensate for swelling of the corneal tissue.

22. The method of claim 21, wherein the corneal tissue increases in thickness in by up to about 50% with the increase from the first hydration to the second hydration.

23. The method of claim 22, wherein the corneal tissue increases in thickness in a range from about 10% to about 50% with the increase in hydration, wherein a first tissue removal depth will effect the desired change in optical property when the eye has the first hydration, and wherein the increased tissue removal depth is between about 10% and about 50% greater than the first tissue removal depth.

24. A method for sculpting of a corneal tissue of an eye to effect a desired change in an optical property of the eye, the method comprising:
    determining the desired change in the optical property while the corneal tissue of the eye has a first hydration;
    sensing a second hydration of the corneal tissue, wherein the eye swells and the hydration increases from the first hydration to the second hydration;
    determining a desired change in shape of the eye in response to the second hydration and the desired change in optical property; and
    planning a pattern of laser energy to direct toward the corneal tissue to effect the determined change in shape.

25. The method of claim 24, wherein the hydration increases and the corneal tissue swells in response to at least one member selected from the group consisting of a therapeutic compound applied to the eye and incising of the eye to expose a tissue for ablation.

26. The method of claim 24, further comprising increasing a total depth of corneal tissue removed from the eye to compensate for swelling of the corneal tissue.

27. The method of claim 26, wherein the corneal tissue increases in thickness in by up to about 50% with the increase from the first hydration to the second hydration.

28. The method of claim 27, wherein the corneal tissue increases in thickness a range from about 10% to about 50% with the increase in hydration, wherein a first tissue removal depth will effect the desired change in optical property when the eye has the first hydration, and wherein the increased tissue removal depth is between about 10% and about 50% greater than the first tissue removal depth.

* * * * *